United States Patent
Chung et al.

(10) Patent No.: US 8,287,627 B2
(45) Date of Patent: Oct. 16, 2012

(54) PIPERAZINIUM TRIFLUOROACETATE COMPOUND AND CARBON DIOXIDE ABSORBENT USING THE SAME

(75) Inventors: Sung Yeup Chung, Seoul (KR); Ki Chun Lee, Seongnam (KR); Seok Jin Choi, Yongin (KR); Hoon Sik Kim, Seoul (KR); Jelliarko Palgunadi, Seoul (KR); Je Eun Kang, Seoul (KR)

(73) Assignee: Hyundai Motor Company, Seoul (KR)

( * ) Notice: Subject to any disclaimer, the term of this patent is extended or adjusted under 35 U.S.C. 154(b) by 293 days.

(21) Appl. No.: 12/612,309

(22) Filed: Nov. 4, 2009

(65) Prior Publication Data

US 2010/0326277 A1 Dec. 30, 2010

(30) Foreign Application Priority Data

Jun. 29, 2009 (KR) .................. 10-2009-0058340

(51) Int. Cl.
*B01D 53/14* (2006.01)

(52) U.S. Cl. .......................................... 95/236; 252/60

(58) Field of Classification Search .................. 252/60, 252/189; 95/235, 236; 544/398, 402, 404
See application file for complete search history.

(56) References Cited

U.S. PATENT DOCUMENTS

| 5,338,846 | A | 8/1994 | Busch et al. | |
|---|---|---|---|---|
| 5,876,488 | A | 3/1999 | Birbara et al. | |
| 6,579,343 | B2 * | 6/2003 | Brennecke et al. | 95/51 |
| 7,208,605 | B2 * | 4/2007 | Davis, Jr. | 548/110 |
| 7,459,134 | B2 * | 12/2008 | Cadours et al. | 423/210 |
| 8,012,277 | B2 * | 9/2011 | Nicolich et al. | 149/22 |
| 2004/0253159 | A1 | 12/2004 | Hakka et al. | |
| 2009/0220397 | A1 * | 9/2009 | Heldebrant et al. | 423/210 |

FOREIGN PATENT DOCUMENTS

| KR | 1020010053250 | 6/2001 |
|---|---|---|
| KR | 10-2006-0124724 A | 5/2006 |

OTHER PUBLICATIONS

Absorption Properties of CO2 in Aqueous Solutions of Piperazine, Piperidine, Cyclohexylamine: Journal of Energy Engineering, vol. 14, No. 4, pp. 219-225 (2005).

* cited by examiner

*Primary Examiner* — Duane Smith
*Assistant Examiner* — Ives Wu
(74) *Attorney, Agent, or Firm* — Edwards Wildman Palmer LLP; Peter F. Corless

(57) ABSTRACT

The present invention provides a novel piperazinium trifluoroacetate compound prepared by reacting piperazine with trifluoroacetic acid and a carbon dioxide absorbent prepared by dissolving the compound in an ionic liquid or organic solvent. According to the present invention, the carbon dioxide absorbent has excellent carbon dioxide absorption capacity and low solvent loss, and the energy consumption required for the carbon dioxide absorption and desorption is significantly reduced.

2 Claims, 4 Drawing Sheets

PIPERAZINIUM TRIFLUOROACETATE COMPOUND AND CARBON DIOXIDE ABSORBENT USING THE SAME

CROSS-REFERENCE TO RELATED APPLICATION

This application claims under 35 U.S.C. §119(a) the benefit of Korean Patent Application No. 10-2009-0058340 filed Jun. 29, 2009, the entire contents of which are incorporated herein by reference.

BACKGROUND (a) Technical Field

The present disclosure relates to a novel piperazinium trifluoroacetate compound and a carbon dioxide absorbent comprising the same.

(b) Background Art

Various methods such as absorption, adsorption, membrane separation, and cryogenic separation are used to separate carbon dioxide from exhaust gas of chemical plants, power plants or large-sized boilers and from natural gas. An absorption or adsorption method is widely used when the concentration of exhausted carbon dioxide is low. The method is industrially used since it can selectively separate a particular gas that can be well absorbed or adsorbed into an absorbent or adsorbent; however, since the absorbent or adsorbent becomes chemically and/or physically inactivated during the separation, it is necessary to periodically replace the absorbent or adsorbent.

An absorption method in which a liquid absorbent is used is widely used in purification of a large amount of exhaust gas or used in gas separation since it is easy to replace the absorbent; however, the liquid absorbent may be chemically and/or physically inactivated.

As carbon dioxide absorbents, amine solutions such as monoethanolamine (MEA), N-methyldiethanolamine (MDEA), diethanolamine (DEA), etc., are widely used since the amine absorbent is chemically combined with carbon dioxide and, when heat is applied thereto, the chemical bond between carbon dioxide and the absorbent is broken such that the carbon dioxide can be stripped and recovered and the absorbent can be recycled. However, this process has several problems such as irreversible decomposition of amine due to high temperature used to break up the chemical bond between carbon dioxide and the absorbent during the recycling process of the absorbent, replenishment of the absorbent, corrosion of an absorption device by amine itself or decomposition products, and contamination of gas recycled by the vapor pressure of the absorbent.

There have been reported various methods of physically absorbing carbon dioxide using organic solvents such as Selexol, IFPexol, NFM, etc. One advantage of the organic solvent absorbents over the aqueous amine absorbents is that there is required a lower energy to recover carbon dioxide and recycle solvents since the absorption of carbon dioxide is achieved by a physical interaction between the solvent and carbon dioxide, not by the chemical bond as in the case of the aqueous amine absorbents. More specifically, in case of the amine absorbent, the recovery of carbon dioxide and the recycling of solvent require an energy-intensive high-temperature stripping process; on the other hand, in case of the physical absorption, it is possible to recover carbon dioxide dissolved in the solvent by simply changing the pressure, not by increasing the temperature.

Nevertheless, the physical absorption method has some drawbacks. For example, since the organic solvent exhibits a carbon dioxide absorption capacity significantly lower than that of an aqueous amine solution, the circulation rate of the absorbent is high, thus necessitating a relatively larger equipment. In addition, since the physical absorption process by the organic solvent requires an absorbent circulation rate much higher than that of the aqueous amine solution, a larger capital and a higher equipment cost are required. Further, since the solvent used in the physical absorption process has a low boiling point, it tends to be lost during the absorption and recycling process.

Various attempts have been made to use as an absorbent a non-volatile ionic liquid having a high thermal stability and maintaining its liquid phase at a low temperature below 100° C., as disclosed in U.S. Pat. No. 6,849,774 B2, U.S. Pat. No. 6,623,659 B2, and U.S. Patent Publication No. 20080146849 A1. The ionic liquid is a salt compound having a polarity and containing an organic cation and an organic or inorganic anion. The solubility of gas absorbed into the ionic liquid varies according to the degree of interaction between the gas and ionic liquid. Therefore, if the polarity, acidity, basicity, and nucleophilicity of the ionic liquid are changed by appropriately changing the cation and anion structures of the ionic liquid, it is possible to adjust the solubility of a specific gas to some extent.

Typically, ionic liquids absorbents contain nitrogen-containing organic cations such as quaternary ammonium including imidazolium, pyrazolium, triazolium, pyridinium, pyridazinium, and pyrimidinium, and anions such as halogens (e.g., $Cl^-$, $Br^-$, and $I^-$), $BF_4^-$, $PF_6^-$, $(CF_3SO)_2N^-$, $CF_3SO_3^-$, $MeSO_3^-$, $NO_3^-$, $CF_3CO_2^-$, and $CH_3CO_2^-$. Especially, it is reported that an anion containing a fluorine atom has a relatively high carbon dioxide absorption capacity. However, these ionic liquid absorbents have problems that the carbon dioxide absorption capacity is significantly low or their manufacturing cost is very high compared to the amine absorbents, thus lowering the economic efficiency.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention provides a novel piperazinium trifluoroacetate compound and a carbon dioxide absorbent using the same, which overcomes the above-listed problems and others as discussed below.

In one aspect, the present invention provides piperazinium trifluoroacetate compounds represented by the following formula 1:

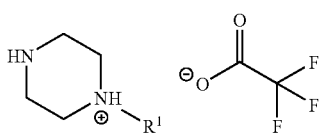

[Formula 1]

wherein $R^1$ represents H or a $C_{1-8}$ alkyl group, a hydroxyl group, or an amine group.

In another aspect, the present invention provides a method of preparing carbon dioxide absorbents from the piperazinium trifluoroacetate compounds.

In still another aspect, the present invention provides a method of absorbing carbon dioxide using the carbon dioxide absorbents.

BRIEF DESCRIPTION OF THE DRAWINGS

The above and other features of the present invention will now be described in detail with reference to certain exemplary embodiments thereof illustrated taken in conjunction with the accompanying drawings which are given hereinbelow by way of illustration only, and thus are not limitative of the present invention, and wherein.

Figure 1:
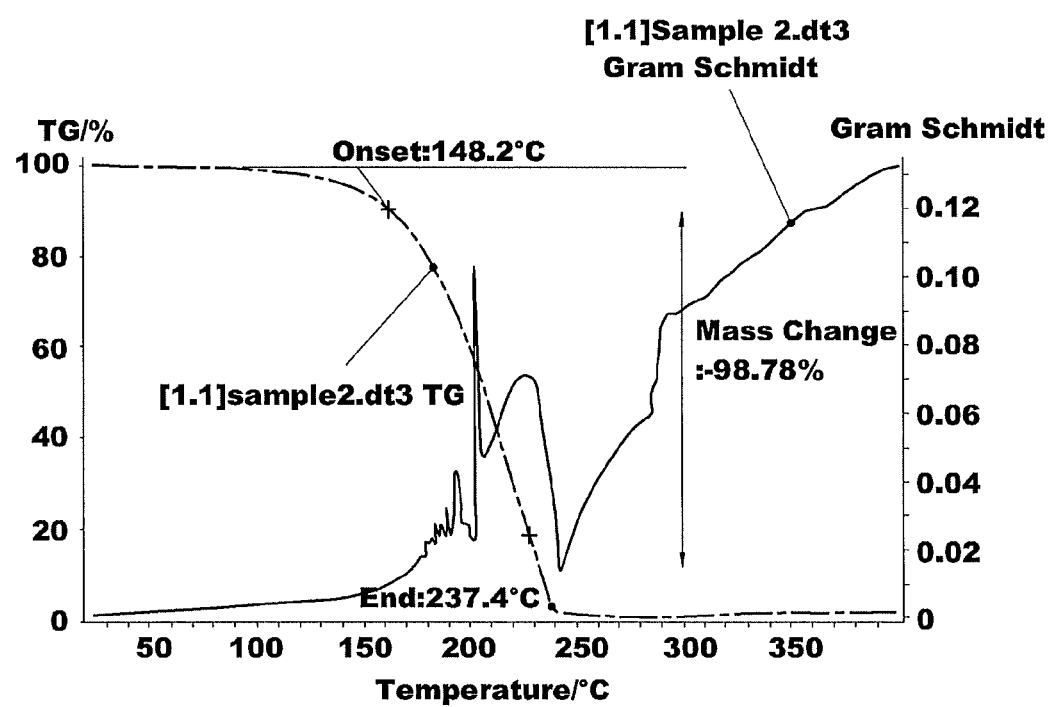
FIG. 1 is a graph showing thermogravimetric analysis (TGA) results of a 1-(2-aminoethyl)piperazinium trifluoroacetate compound prepared in Synthesis Example 1.

Reference numerals set forth in the Drawings includes reference to the following elements as further discussed below:

S1: $CO_2$ supply cylinder
S2: $CO_2$ storage cylinder
R1: stainless steel absorption reactor
P1: high-pressure transducer
P2: manometer
T1, T2: thermometer
1: stirrer It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, the present invention will be described in detail with reference to the accompanying drawings.

The present invention relates to a piperazinium trifluoroacetate compound represented by the following formula 1 and a carbon dioxide absorbent prepared using the compound, which can minimize solvent loss and reduce energy consumption:

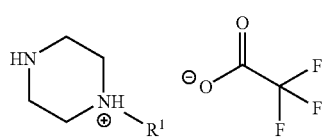

[Formula 1]

wherein $R^1$ represents H or a $C_{1-8}$ alkyl group, a hydroxyl group, or an amine group.

The piperazinium trifluoroacetate compound is prepared by reacting piperazine with trifluoroacetic acid.

The piperazine has a structure represented by the following formula 2:

[Formula 2]

wherein $R^1$ represents H or a $C_{1-8}$ alkyl group, a hydroxyl group, or an amine group.

The piperazine may include at least one selected from the group consisting of 1-methylpiperazine (MePz), 1-ethylpiperazine (EtPz), 1-(2-aminoethyl)piperazine (AmEtPz), and 1-(2-hydroxyethyl)piperazine (HyEtPz).

In the synthesis of the piperazinium trifluoroacetate compound, the amount of trifluoroacetic acid with respect to the piperazine varies according to the number of amine groups of the piperazine, and the trifluoroacetic acid in an amount capable of converting at least one amine group into a corresponding ammonium group is required. Preferably, the molar ratio of the piperazine to trifluoroacetic acid is 1:0.25 to 1:0.75, which may, however, vary according to the number of amine groups of the piperazine. For example, if the piperazine contains secondary amine groups, at least 0.5 mol of trifluoroacetic acid is required, and preferably 0.5 to 0.7 mol of trifluoroacetic acid is required. If the amount of trifluoroacetic acid is more than 0.7 mol, the viscosity of the final absorbent increases, and thus the carbon dioxide absorption capacity is reduced. In the case of 1-(2-aminoethyl)piperazine (AmEtPz) containing tertiary amine groups, 0.33 to 0.67 mol of trifluoroacetic acid per mole of piperazine is suitable. If the amount of trifluoroacetic acid is less than 0.33 mol, 1-(2-aminoethyl)piperazine in which all of the amine groups are not converted into ammonium groups is present, and thus a lot of energy is required during desorption of carbon dioxide. Whereas, if the amount of trifluoroacetic acid is more than 0.67 mol, the number of free amine groups may be reduced, and thus the carbon dioxide absorption capacity is reduced. In the case of 1,4-diaminoethylpiperazine containing quaternary amine groups, 0.25 to 0.75 mol of trifluoroacetic acid per mole of piperazine is suitable.

A carbon dioxide absorbent according to the present invention can be prepared by dissolving the novel piperazinium trifluoroacetate compound in an ionic liquid or organic solvent. The amount of piperazinium trifluoroacetate used in the preparation of the absorbent may be 3 to 60 wt. % of the total weight of the solution, and preferably 10 to 40 wt. %. If the amount of piperazinium trifluoroacetate is less than 3 wt. %, the improvement effect of the carbon dioxide absorption capacity by the addition of piperazinium trifluoroacetate may be reduced. Whereas, if the amount of piperazinium trifluoroacetate is more than 60 wt. %, the viscosity of the final absorbent may excessively increase, thus causing a lot of problems in the absorption process.

The ionic liquid used to dissolve the piperazinium trifluoroacetate may include at least one selected from the group consisting of dimethylimidazolium dimethylphosphate (DMIM $DMPO_4$), dimethylimidazolium methylphosphite (DMIM $MHPO_3$), ethylmethylimidazolium diethylphosphate (EMIM $DEPO_4$), ethylmethylimidazolium ethylphosphite (EMIM $EHPO_3$), diethylimidazolium diethylphosphate (DEIM DEPO$_4$), diethylimidazolium ethylphosphite (DEIM EHPO$_3$), ethylmethylimidazolium dimethylphosphate (EMIM DMPO$_4$), ethylmethylimidazolium methylphosphite (EMIM MHPO$_3$), butylmethylimidazolium dimethylphosphate (BMIM DMPO$_4$), butylmethylimidazolium methylphosphite (BMIM MHPO$_3$), butylmethylimidazolium dibutylphosphate (BMIM DBPO$_4$), butylmethylimidazolium butylphosphite (BMIM BHPO$_3$), butylethylimidazolium dibutylphosphate (BEIM DBPO$_4$), butylethylimidazolium butylphosphite (BEIM BHPO$_3$), butylethylimidazolium diethylphosphate (BEIM DEPO$_4$), butylethylimidazolium ethylphosphite (BEIM EHPO$_3$), dibutylimidazolium dibutylphosphate (DBIM DBPO$_4$), and dibutylimidazolium butylphosphite (DBIM BHPO$_3$).

The organic solvent used to dissolve the piperazinium trifluoroacetate may include at least one selected from the group consisting of dimethylacetamide (DMAc), ethylene glycol (EG), and dimethylformamide (DMF).

When the carbon dioxide is absorbed into the ionic liquid in which the piperazinium trifluoroacetate of the invention is dissolved, the temperature may be in the range of −20 to 80° C., preferably in the range of 20 to 50° C., and the pressure may be in the range of normal pressure to 100 atm, preferably in the range of normal pressure to 30 atm. Then, the absorbed carbon dioxide may be desorbed at a temperature in the range of 20 to 120° C., preferably in the range of 40 to 80° C., and at a pressure in the range of 0 to 10 atm, preferably in the range of 0 to normal pressure. During the absorption of carbon dioxide, if the temperature and the pressure are out of the above ranges, the efficiency of the carbon dioxide absorption process is reduced. In general, the amount of carbon dioxide absorbed increases at a lower temperature and at a higher pressure. Especially, if the absorption pressure increases, the amount of carbon dioxide absorbed is increased substantially linearly proportional to the increase in pressure.

[Evaluation of Carbon Dioxide Absorption/Desorption Capacities]

Figure 3:
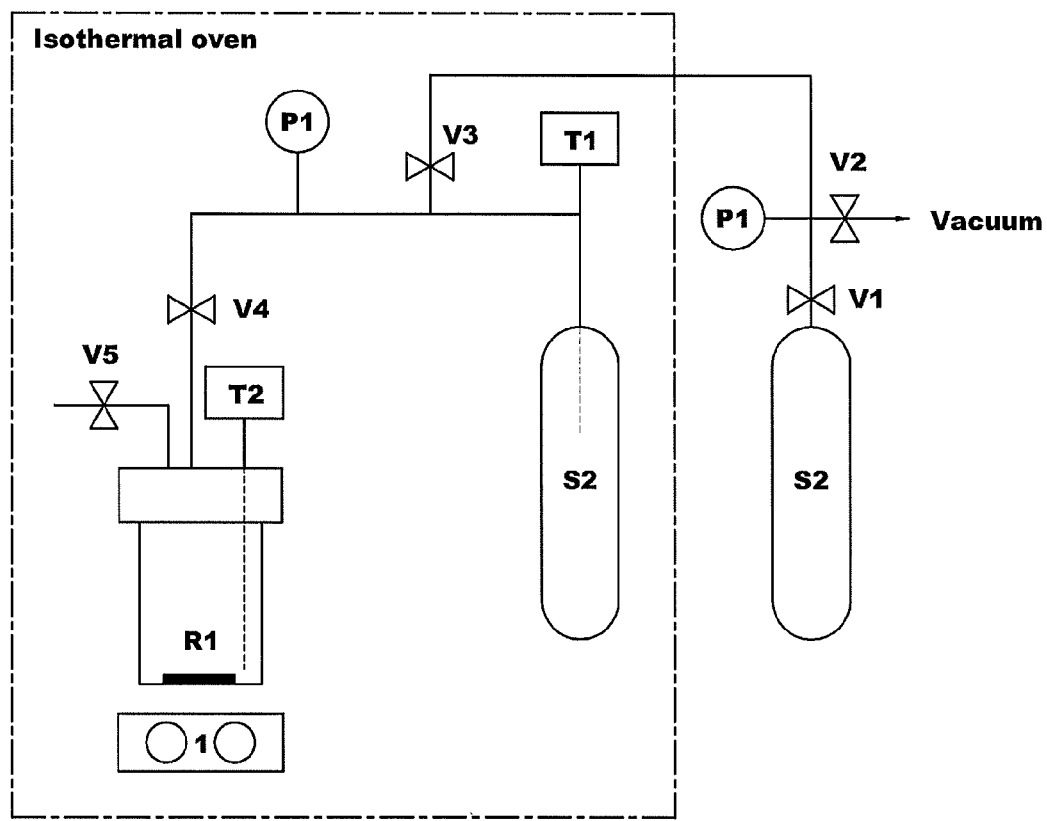
FIG. 3 is a schematic diagram of a carbon dioxide absorption/desorption capacity tester.

The configuration of a carbon dioxide absorption/desorption capacity tester used to evaluate the carbon dioxide absorption/desorption capacities of the novel absorbent in accordance with the present invention is shown in FIG. 3. The carbon dioxide absorption/desorption capacity tester includes a 60 ml stainless steel absorption reactor R1 equipped with a thermometer T2, a high-pressure transducer P1 (0 to 1,500 psi), a 75 ml CO$_2$ storage cylinder S2 equipped with a thermometer T1, and a stirrer 1, and is installed in an isothermal oven to measure the carbon dioxide absorption/desorption capacities at a constant temperature.

A carbon dioxide absorption/desorption capacity test was performed in the following manner. After weighing, the prepared ionic liquid was put into the stainless steel absorption reactor R1 of FIG. 3 together with a magnet bar, stirred at 40 to 80° C. for one hour, and dried under vacuum. After turning off a valve V4 connected to the stainless steel absorption reactor R1, carbon dioxide at a constant pressure (e.g., 50 to 60 psig) was put into the CO$_2$ storage cylinder S2. Then, after the CO$_2$ storage cylinder S2 was maintained in equilibrium, the pressure and temperature were recorded (initial values). In the same manner, after turning on the valve V4, the pressure and temperature in equilibrium were recorded, and the CO$_2$ storage cylinder S2 was stirred. After 30 minutes, the final pressure and temperature were recorded (equilibrium values). After turning off the valve V4, the pressure was slowly increased (60 to 1,500 psig), and the initial and equilibrium values were measured four to ten times. During desorption test, a valve V5 was turned on after the carbon dioxide absorption test, the pressure was reduced, and the temperature was increased to 70° C., thus desorbing the absorbed carbon dioxide.

The operation principle of the tester shown in FIG. 3 is similar to that generally used in the physical absorption process. The desorption process of the carbon dioxide absorbed into the absorbent requires a lower energy than a high-temperature recycling process in which a primary amine absorbent such as ethanolamine or diethanolamine is used to recover carbon dioxide. The reason for this is that, unlike the ethanolamine or diethanolamine, in the case of the piperazinium, since secondary or tertiary amine groups react with trifluoroacetate to be converted into quaternary ammonium cations, unshared electron pairs of unconverted primary or secondary amine groups migrate through the cation, and thus the electron density of the amine group, i.e., the basicity is reduced, which results in a reduction in chemical bonding strength with carbon dioxide known as carbonic acid gas.

Since the absorbent in accordance with the present invention contains constituents having a very low vapor pressure, the possibility of losing the absorbent is low and, since the absorbent is chemically stable, the possibility of losing the absorbent in the desorption process is also low. Moreover, the other ionic liquid used in a predetermined amount to dissolve the piperazinium trifluoroacetate in a solid state can dissolve ammonium carbamate generated when the piperazinium trifluoroacetate reacts with carbon dioxide, and thus it is more efficient in terms of energy consumption compared to the amine absorbents and physical absorbents, which use aqueous solutions. Furthermore, since the carbon dioxide absorbent using the piperazinium trifluoroacetate in accordance with the present invention has carbon dioxide absorption/desorption capacities higher than those of the other physical absorbents, it is possible to reduce the amount of absorbent used and the circulation rate, thus reducing the size of the equipment.

The present invention will be described in more detail with reference to the following Synthesis Examples, Examples, and Test Examples; however, the present invention is not limited to these examples.

SYNTHESIS EXAMPLES

Synthesis of Piperazinium Trifluoroacetate Compound

Synthesis Example 1

12.92 g (0.1 mol) of 1-(2-aminoethyl)piperazine and 50 g of ethylene glycol or acetonitrile as an organic solvent were put into a 250 ml two-necked flask equipped with a condenser, and 11.4 g (0.1 mol) of trifluoroacetic acid was slowly added dropwise thereto. The resulting solution was stirred at room temperature for 4 hours, washed with diethyl ether several times, and then dried under vacuum, thus obtaining 1-(2-aminoethyl)piperazinium trifluoroacetate (yield: 86%).

Synthesis Example 2

1-(2-aminoethyl)piperazinium trifluoroacetate was prepared in the same manner as Synthesis Example 1, except that 22.8 g (0.2 mol) of trifluoroacetic acid was added such that the molar ratio of 1-(2-aminoethyl)piperazine to trifluoroacetic acid was 1:2.

EXAMPLES

Preparation of Carbon Dioxide Absorbents

Example 1

6 g of 1-(2-aminoethyl)piperazinium trifluoroacetate obtained in Synthesis Example 1 was dissolved in 14 g of dimethylimidazolium methylphosphite as an ionic liquid at 40° C. for more than 30 minutes, thus preparing a carbon dioxide absorbent.

Example 2

6 g of 1-(2-aminoethyl)piperazinium trifluoroacetate obtained in Synthesis Example 1 was dissolved in 14 g of dimethylformamide as an organic solvent at 30° C. for more than 30 minutes, thus preparing a carbon dioxide absorbent.

TEST EXAMPLES

Test Example 1

Measurement of Thermal Stability of Piperazinium Trifluoroacetate Compound [Thermogravimetric Analysis (Tga)]

Figure 2:
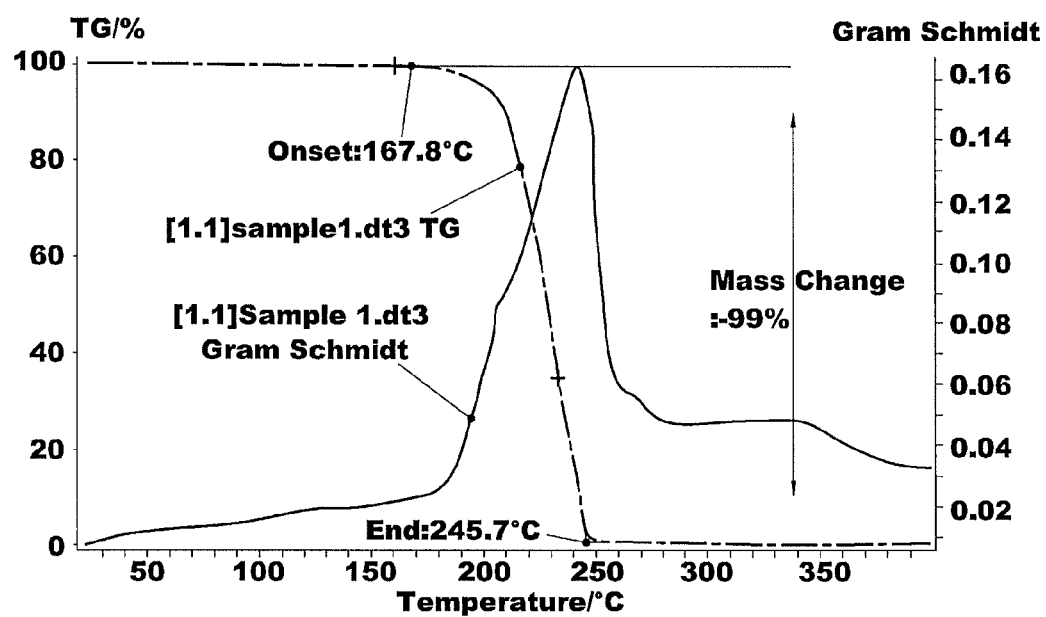
FIG. 2 is a graph showing TGA results of a 1-(2-aminoethyl)piperazinium trifluoroacetate compound prepared in Synthesis Example 2.

Thermogravimetric analysis (TGA) was performed on the piperazinium trifluoroacetate prepared in Synthesis Examples 1 and 2 to measure their thermal stability, and the results of Synthesis Examples 1 and 2 are shown in FIGS. 1 and 2, respectively.

As shown in FIGS. 1 and 2, the decomposition onset temperature of the compound prepared in Synthesis Example 1 was 148.2° C. and that of the compound prepared in Synthesis Example 2 was 167.8° C., from which it can be seen that the compounds prepared in Synthesis Examples 1 and 2 have significant thermal stability compared to water or amine compounds and no deterioration occurs when the absorbent is recycled below 100° C.

Evaluation of Carbon Dioxide Absorption/Desorption Capacities

Test Example 2

Figure 4:
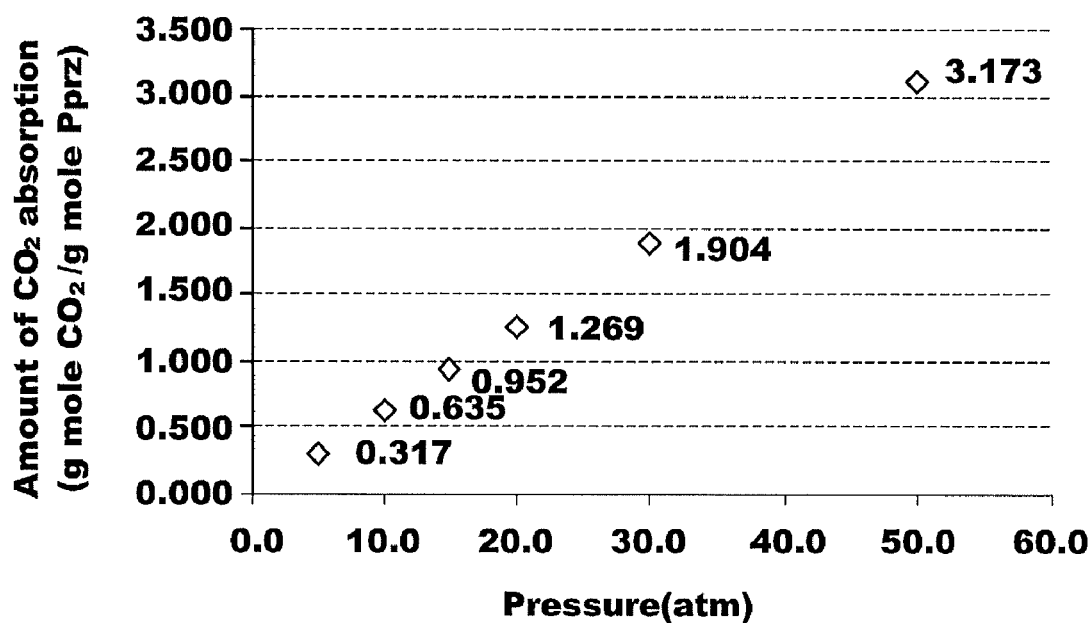
FIG. 4 is a graph showing the amounts of carbon dioxide absorbed (at 40° C., 30 wt. %) into a 1-(2-aminoethyl)piperazinium trifluoroacetic acid compound according to a change in pressure.

A carbon dioxide absorption test was performed on the carbon dioxide absorbent prepared in Example 1 using the carbon dioxide absorption/desorption capacity tester shown in FIG. 3 installed in an isothermal oven of which the temperature was maintained at 40° C. After filling the $CO_2$ storage cylinder S2 with carbon dioxide at a constant pressure, the valve V4 was turned off such that the carbon dioxide gas expands in the stainless steel absorption reactor R1 and thus the initial pressure of the stainless steel absorption reactor R1 and the overall system became 1 atm. Then, the degree that the pressure of the $CO_2$ storage cylinder S2 was reduced was estimated until the absorption equilibrium was reached, and the amount of carbon dioxide dissolved in dimethylimidazolium methylphosphite as an ionic liquid was measured using a gas state equation. In the same manner, the pressure of the overall system was increased such that the initial carbon dioxide pressure of the stainless steel absorption reactor R1 became 5, 10, 15, 30, and 50 atm, respectively, and the amounts of carbon dioxide absorbed according to the change in pressure were measured. As shown in FIG. 4, the amount of carbon dioxide absorbed was increased in proportion to the increase in carbon dioxide pressure.

Test Examples 3 to 6

Amounts of Carbon Dioxide Absorbed According to a Change in Absorption Temperature Carbon dioxide absorption tests were performed in the same manner as Test Example 2, except that the pressure was fixed at 15 atm and the absorption temperature was changed as shown in Table 1. The results of the carbon dioxide absorption tests are shown in Table 1:

TABLE 1

| Test Example | Carbon dioxide absorbent | Absorption temperature (° C.) | Amount of $CO_2$ absorbed (gmol $CO_2$/gmol absorbent) |
|---|---|---|---|
| 3 | Example 1 | 20 | 1.44 |
| 4 | | 30 | 1.22 |
| 5 | | 50 | 0.71 |
| 6 | | 60 | 0.52 |

Test Examples 7 to 10

Amounts of Carbon Dioxide Absorbed According to a Change in the Type of Piperazinium Compounds Carbon dioxide absorption tests were performed in the same manner as Test Example 3, except that the temperature was fixed at 40° C., the pressure was fixed at 15 atm, and the type of piperazinium compound was changed as shown in Table 2. The results of the carbon dioxide absorption tests are shown in Table 2:

TABLE 2

| Test Example | Carbon dioxide absorbent | Piperazinium (30 wt %) | Amount of $CO_2$ absorbed (gmol $CO_2$/gmol piperazinium) |
|---|---|---|---|
| 7 | Example 1 | PzH $CF_3CO_2$ | 0.83 |
| 8 | | MePzH $CF_3CO_2$ | 0.88 |
| 9 | | EtPzH $CF_3CO_2$ | 0.90 |
| 10 | | HyEtPzH $CF_3CO_2$ | 0.80 |

Test Examples 11 to 18

Amounts of Carbon Dioxide Absorbed According to a Change in the Type of Ionic Liquids Carbon dioxide absorption tests were performed in the same manner as Test Example 3, except that the temperature was fixed at 40° C., the pressure was fixed at 15 atm, and the type of ionic liquid was changed as shown in Table 3. The results of the carbon dioxide absorption tests are shown in Table 3:

TABLE 3

| Test Examples | Carbon dioxide absorbent | Ionic liquid | Amount of $CO_2$ absorbed (gmol $CO_2$/gmol absorbent) |
|---|---|---|---|
| 11 | Example 1 | DMIM DMPO$_4$ | 0.83 |
| 12 | | EMIM EHPO$_3$ | 0.97 |
| 13 | | EMIM MHPO$_3$ | 0.96 |
| 14 | | DEIM DEPO$_4$ | 0.77 |
| 15 | | BMIM BHPO$_3$ | 0.98 |
| 16 | | BMIM DMPO$_4$ | 0.77 |
| 17 | | BEIM DEPO$_4$ | 0.75 |
| 18 | | DMIM BHPO$_3$ | 0.98 |

Test Examples 19 to 22

Amounts of Carbon Dioxide Absorbed According to a Change in the Amount of Piperazinium Carbon dioxide absorption tests were performed in the same manner as Test Example 3, except that the ionic liquid was fixed to dimethylimidazolium methylphosphite, the temperature was fixed at 40° C., the pressure was fixed at 15 atm, and the amount of piperazinium with respect to the ionic liquid was changed as shown in Table 4. The results of the carbon dioxide absorption tests are shown in Table 4:

TABLE 4

| Test Example | Carbon dioxide absorbent | Amount of piperazinium (wt %) | Amount of $CO_2$ absorbed (gmol $CO_2$/gmol piperazinium) |
|---|---|---|---|
| 19 | Example 1 | 5 | 0.45 |
| 20 | | 10 | 0.64 |
| 21 | | 20 | 0.76 |
| 22 | | 40 | 1.32 |

Test Examples 23 to 26

Amounts of Carbon Dioxide Absorbed According to a Change in the Reaction Molar Ratio of Trifluoroacetic Acid to Piperazine Carbon dioxide absorption tests were performed in the same manner as Test Example 3, except that 1-(2-aminoethyl)piperazinium trifluoroacetic acid compounds were prepared by varying the molar ratio of trifluoroacetic acid to 1-(2-aminoethyl)piperazine as shown in Table 5, in which the ionic liquid was fixed to dimethylimidazolium methylphosphite, the temperature was fixed at 40° C., the pressure was fixed at 20 atm. The results of the carbon dioxide absorption tests are shown in Table 5:

TABLE 5

| Test Example | Carbon dioxide absorbent | Molar ratio ($CF_3CO_2H$/piperazine) | Amount of $CO_2$ absorbed (gmol $CO_2$/gmol piperazinium) |
|---|---|---|---|
| 23 | Example 1 | 0.33 | 1.24 |
| 24 | | 0.50 | 1.07 |
| 25 | | 0.67 | 0.89 |
| 26 | | 0.75 | 0.68 |

Test Examples 27 to 36

Amounts of Carbon Dioxide Absorbed According to Changes in the Type of Ionic Liquids, the Absorption Pressure, and the Absorption Temperature Carbon dioxide absorption tests were performed in the same manner as Test Example 3, except that after absorbing carbon dioxide at 10 or 20 atm and at 30° C. while changing the types of piperazinium and ionic liquid as shown in Table 6, the equilibrium values were measured, and the pressure was returned to normal pressure such that the resulting carbon dioxide was desorbed at 40 to 80° C. Upon the first completion of the carbon dioxide absorption and desorption, the carbon dioxide absorption and desorption processes was repeated under the same conditions ten times. The comparison results between the first absorption capacity and the tenth absorption capacity are shown in Table 6:

TABLE 6

| Test Example | [piperazinium] [$CF_3CO_2$] | Ionic liquid | Absorption Pressure (atm) | Desorption Temperature (° C.) | Amount of $CO_2$ absorbed (gmol/gmol absorbent) First absorption | Tenth absorption |
|---|---|---|---|---|---|---|
| 27 | [AmEtPzH] [$CF_3CO_2$] | DMIM DMPO$_4$ | 10 | 70 | 0.79 | 0.78 |
| 28 | [AmEtPzH] [$CF_3CO_2$] | DEIM EHPO$_3$ | 20 | 70 | 1.34 | 1.28 |
| 29 | [MePzH] [$CF_3CO_2$] | BMIM MHPO$_3$ | 10 | 70 | 0.63 | 0.60 |
| 30 | [MePzH] [$CF_3CO_2$] | BMIM DBPO$_4$ | 20 | 70 | 1.10 | 1.00 |
| 31 | [EtPzH] [$CF_3CO_2$] | BEIM DBPO$_4$ | 10 | 70 | 0.70 | 0.68 |
| 32 | [EtPzH] [$CF_3CO_2$] | EMIM DEPO$_4$ | 20 | 70 | 1.18 | 1.07 |
| 33 | [PzH] [$CF_3CO_2$] | EMIM DMPO$_4$ | 10 | 70 | 0.59 | 0.59 |

TABLE 6-continued

| Test Example | [piperazinium] [$CF_3CO_2$] | Ionic liquid | Absorption Pressure (atm) | Desorption Temperature (° C.) | Amount of $CO_2$ absorbed (gmol/gmol absorbent) First absorption | Tenth absorption |
|---|---|---|---|---|---|---|
| 34 | [PzH] [$CF_3CO_2$] | BEIM $BHPO_3$ | 20 | 70 | 0.88 | 0.86 |
| 35 | [AmEtPzH$_2$] [$CF_3CO_2$]$_2$ | BEIM $EHPO_3$ | 10 | 80 | 0.70 | 0.66 |
| 36 | [AmEtPzH$_2$] [$CF_3CO_2$]$_2$ | DBIM $DBPO_4$ | 10 | 40 | 1.11 | 1.10 |

Test Examples 37 to 39

Amounts of Carbon Dioxide Absorbed According to a Change in the Type of Organic Solvent Carbon dioxide absorption tests were performed in the same manner and under the same conditions as Test Example 3, except that the pressure was fixed at 7 atm and carbon dioxide was dissolved in various types of organic solvents as shown in Table 7. The results of the carbon dioxide absorption tests performed at 40° C. are shown in Table 7:

TABLE 7

| Test Example | Organic solvent | Amount of $CO_2$ absorbed (gmol $CO_2$/gmol absorbent) |
|---|---|---|
| 37 | DMAc | 0.167 |
| 38 | EG | 0.33 |
| 39 | DMF | 0.55 |

Comparison with Existing Carbon Dioxide Absorbents

Test Example 40

Amount of Carbon Dioxide Absorbed into Diethanolamine Absorbent

A carbon dioxide absorption test, in which carbon dioxide was absorbed into a diethanolamine absorbent, widely used among the amine absorbents, was performed at 1 atm and at 30° C., and the absorbed carbon dioxide was desorbed from the diethanolamine absorbent at normal pressure and at 110° C. This experiment was repeated two times. During the first absorption, 0.177 gmol/gmol of carbon dioxide was absorbed into the absorbent; however, during the second absorption, 0.144 gmol/gmol was absorbed, which resulted in a 19% reduction in the absorption capacity of the absorbent.

Test Example 41

Amount of Carbon Dioxide Absorbed into Dimethylimidazolium Methylphosphite Absorbent In the same manner as Test Example 3, a carbon dioxide absorption test was performed using the ionic liquid dimethylimidazolium methylphosphite as a sole absorbent to absorb carbon dioxide at 15 atm and at 40° C., and as a result, 0.142 mol of carbon dioxide was absorbed into 1 mol of dimethylimidazolium methylphosphite, which was significantly lower compared to the case where 30 wt % of piperazinium trifluoroacetate was dissolved (refer to Test Example 2).

Test Example 42

A carbon dioxide absorption test was performed at a fixed pressure of 7 atm and at 40° C. using organic solvent dimethylacetamide (DMAc), ethylene glycol (EG), and dimethylformamide (DMF) as a sole absorbent, respectively, and as a result, the amount of carbon dioxide absorbed into dimethylacetamide was 0.109 gmol, the amount of carbon dioxide absorbed into ethylene glycol was 0.016 gmol, and the amount of carbon dioxide absorbed into dimethylformamide was 0.097, which were significantly lower compared to the case where 30 wt % of piperazinium trifluoroacetate was dissolved (refer to Test Examples 37 to 39).

From the above-described examples, it can be seen that the carbon dioxide absorbent containing the piperazinium trifluoroacetate compound in accordance with the present invention exhibits excellent absorption capacity, that the absorbed carbon dioxide is easily desorbed, and that the absorption capacity is maintained substantially the same as the initial level after repeated use. For example, in the case where carbon dioxide was absorbed at 15 atm and at 40° C. into a solution in which 30 wt % of 1-(2-aminoethyl)piperazinium trifluoroacetate prepared by reacting 1-(2-aminoethyl)piperazine with trifluoroacetic acid of the same equivalent weight and 70 wt % of another ionic liquid dimethylimidazolium methylphosphite were dissolved, the equilibrium state was reached within 30 minutes, which corresponded to 0.952 mol of carbon dioxide absorbed per mole of the absorbent and a value approximately two times the theoretical maximum absorption capacity of the amine absorbent, 0.5 mol of carbon dioxide absorbed per mole of amine. In this case, the equilibrium value corresponds to an absorption value when the amount of carbon dioxide measured with the lapse of time is no longer changed. When a carbon dioxide absorption test was repeated under the same conditions after the carbon dioxide desorption process in which the pressure was returned to normal pressure and the temperature was increased to 70° C. after the amount of carbon dioxide reached the equilibrium value, the amount of carbon dioxide absorbed per mole of the absorbent was 0.950 mol after 30 minutes. Moreover, even after repeating the carbon dioxide absorption and desorption processes ten times, the final absorption capacity was not different from the initial absorption capacity. Compared to this, according to the results of Test Examples 37, in which carbon dioxide was absorbed into diethanolamine, typically used as a carbon dioxide absorbent among the existing amine compounds, at 1 atm and at 40° C., and the absorbed carbon dioxide was desorbed at normal pressure and at 110° C., which were repeated under the same conditions two times, the final absorption capacity was reduced by about 15% compared to the initial absorption capacity. Therefore, when the absorbent containing a predetermined amount of piperazinium trifluoroacetate in accordance with the present invention is used, the energy consumption required to recycle the absorbent is significantly reduced compared to the existing amine absorption process. Moreover, since the absorbent of the invention can absorb, desorb, and separate carbon dioxide repeatedly for a long time, it is possible to significantly reduce the overall energy consumption required for such processes.

As described above, according to the present invention, an absorbent in which a piperazinium trifluoroacetate compound is dissolved in an ionic liquid does not require water as a solvent, has little vapor pressure, exhibits excellent thermal stability, and easily absorbs carbon dioxide. Moreover, the carbon dioxide absorbed into the absorbent can be easily desorbed at a relatively low temperature, and even when the carbon dioxide absorption and desorption are repeatedly performed, the initial absorption capacity can be maintained as it is. Furthermore, since the absorbent of the invention has excellent carbon dioxide absorption capacity compared to existing amine absorbents, it can be used as an effective carbon dioxide separation medium.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A carbon dioxide absorbent prepared by dissolving 3 to 60 wt. % of a piperazinium trifluoroacetate compound represented by the following formula 1 in an ionic liquid:

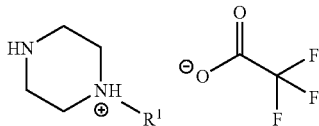

[Formula 1]

wherein $R^1$ represents H or a $C_{1-8}$ alkyl group, a hydroxyl group, or an amine group, and wherein the ionic liquid comprises at least one selected from the group consisting of dimethylimidazolium dimethylphosphate, dimethylimidazolium methylphosphite, ethylmethylimidazolium diethylphosphate, ethylmethylimidazolium ethylphosphite, diethylimidazolium diethylphosphate, diethylimidazolium ethylphosphite, ethylmethylimidazolium dimethylphosphate, ethylmethylimidazolium methylphosphite, butylmethylimidazolium dimethylphosphate, butylmethylimidazolium methylphosphite, butylmethylimidazolium dibutylphosphate, butylmethylimidazolium butylphosphite, butylethylimidazolium dibutylphosphate, butylethylimidazolium butylphosphite, butylethylimidazolium diethylphosphate, butylethylimidazolium ethylphosphite, dibutylimidazolium dibutylphosphate, and dibutylimidazolium butylphosphite.

2. A method of absorbing carbon dioxide using a carbon dioxide absorbent of claim 1 at an absorption temperature of −20 to 80° C., at a desorption temperature of 20 to 120° C., at an absorption pressure from normal pressure to 100 atm, and at a desorption pressure from 0 to 10 atm.

* * * * *

UNITED STATES PATENT AND TRADEMARK OFFICE
CERTIFICATE OF CORRECTION

| | | |
|---|---|---|
| PATENT NO. | : 8,287,627 B2 | |
| APPLICATION NO. | : 12/612309 | |
| DATED | : October 16, 2012 | |
| INVENTOR(S) | : Sung Yeup Chung et al. | |

It is certified that error appears in the above-identified patent and that said Letters Patent is hereby corrected as shown below:

On the title page of the patent, at Column 1, in the section designated "ASSIGNEE" Item (73) please add -- Kia Motors Corporation, Seoul, KR --

Signed and Sealed this
Fourteenth Day of May, 2013

Teresa Stanek Rea
*Acting Director of the United States Patent and Trademark Office*